US00PP31826P2

(12) United States Plant Patent

Sills et al.

(10) Patent No.: US PP31,826 P2
(45) Date of Patent: Jun. 2, 2020

(54) BLACKBERRY PLANT VARIETY NAMED 'DRISBLACKTWENTY'

(50) Latin Name: ***Rubus* L. subgenus *Rubus***
Varietal Denomination: DrisBlackTwenty

(71) Applicant: Driscoll's, Inc., Watsonville, CA (US)

(72) Inventors: Gavin R. Sills, Gilroy, CA (US); Mark F. Crusha, Capitola, CA (US); Missael Bonifacio Romero Escobedo, Ciudad Guzmán (MX)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,447

(22) Filed: Apr. 17, 2019

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./156, 203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| 2016/0249505 | P1 | 8/2016 | Sills et al. |

OTHER PUBLICATIONS

Sills et al., Unpublished U.S. Appl. No. 15/932,943, filed May 24, 2018, titled "Blackberry Plant Named 'DrisBlackSeventeen'".
Sills et al., Unpublished U.S. Appl. No. 15/998,320, filed Aug. 3, 2018, titled "Blackberry Plant Variety Named 'DrisBlackEighteen'".
Sills et al., Unpublished U.S. Appl. No. 16/501,448, filed Apr. 17, 2019, titled "Blackberry Plant Variety Named 'DrisBlackNineteen'".
Voss, Donald H. "The Royal Horticultural Society Colour Chart 2001", Journal American Rhododendron Society, vol. 56, No. 1, 2002, 3 pages.
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Susan McCormick Ewoldt
*Assistant Examiner* — Karen M Redden
(74) *Attorney, Agent, or Firm* — Morrison & Foerster LLP

(57) ABSTRACT

A new and distinct variety of blackberry plant named 'DrisBlackTwenty', particularly characterized by its plant vigor, yield, fruit shelf-life, and flavor, is disclosed.

5 Drawing Sheets

Latin name:
Botanical classification: *Rubus* L. subgenus *Rubus*.
Varietal denomination:
The varietal denomination of the claimed variety of blackberry plant is 'DrisBlackTwenty'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed by the University of Arkansas capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackTwenty'.

Blackberry plant variety 'DrisBlackTwenty' was selected in Los Reyes, Mexico in March of 2011 and originated from a cross between the proprietary female parent blackberry plant 'BN843.2' (unpatented) and the proprietary male parent blackberry plant 'BL481.3' (unpatented). The original seedling of the new variety was first asexually propagated via root cuttings in Los Reyes, Mexico in March of 2011.

'DrisBlackTwenty' was subsequently asexually propagated via root cuttings, and underwent testing at a test plot in Los Reyes, Mexico from 2012 to 2018 for 6 years. The present variety has been found to be stable and reproduce true to type through successive asexual propagations via root cuttings.

'DrisBlackTwenty' exhibits the following distinguishing characteristics over other similar varieties when grown under normal horticultural practices in Los Reyes, Mexico:

1. Upright to semi-upright plant growth habit;
2. No spines on dormant cane; and
3. Absent or few glandular hairs on young shoot.

'DrisBlackTwenty' was selected for its plant vigor, yield, fruit shelf-life, and flavor.

BRIEF DESCRIPTION OF THE DRAWINGS

This new blackberry plant is illustrated by the accompanying photographs, which show fruit of the plant, flowers, a leaf, a cane, and a plant. The colors shown are as true as can be reasonably obtained by conventional photographic procedures. The photographs are of plants that are three years old.

DETAILED BOTANICAL DESCRIPTION

Figure 1:
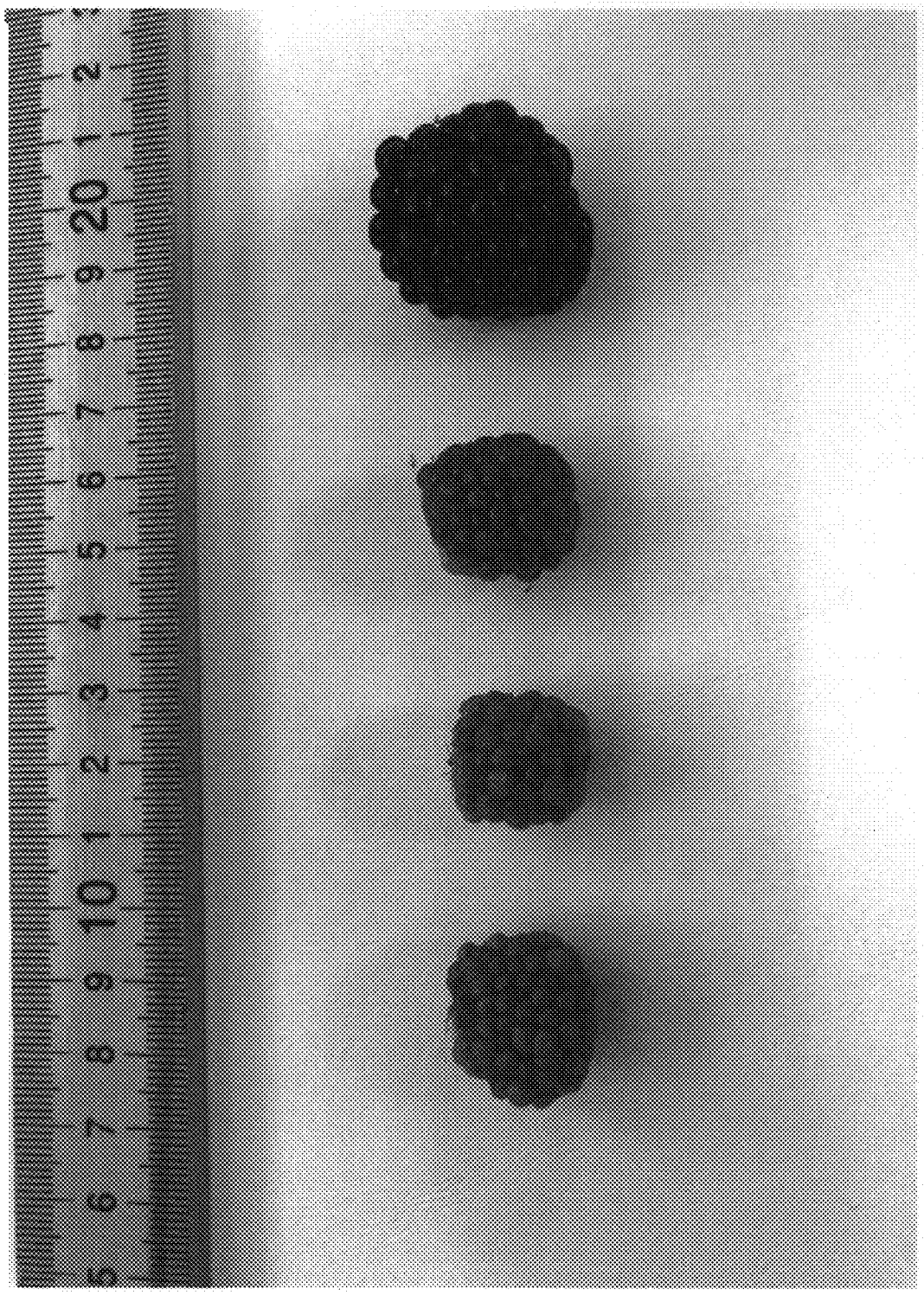
FIG. 1 illustrates typical fruit of variety 'DrisBlackTwenty' at various stages of development.
Figure 2:
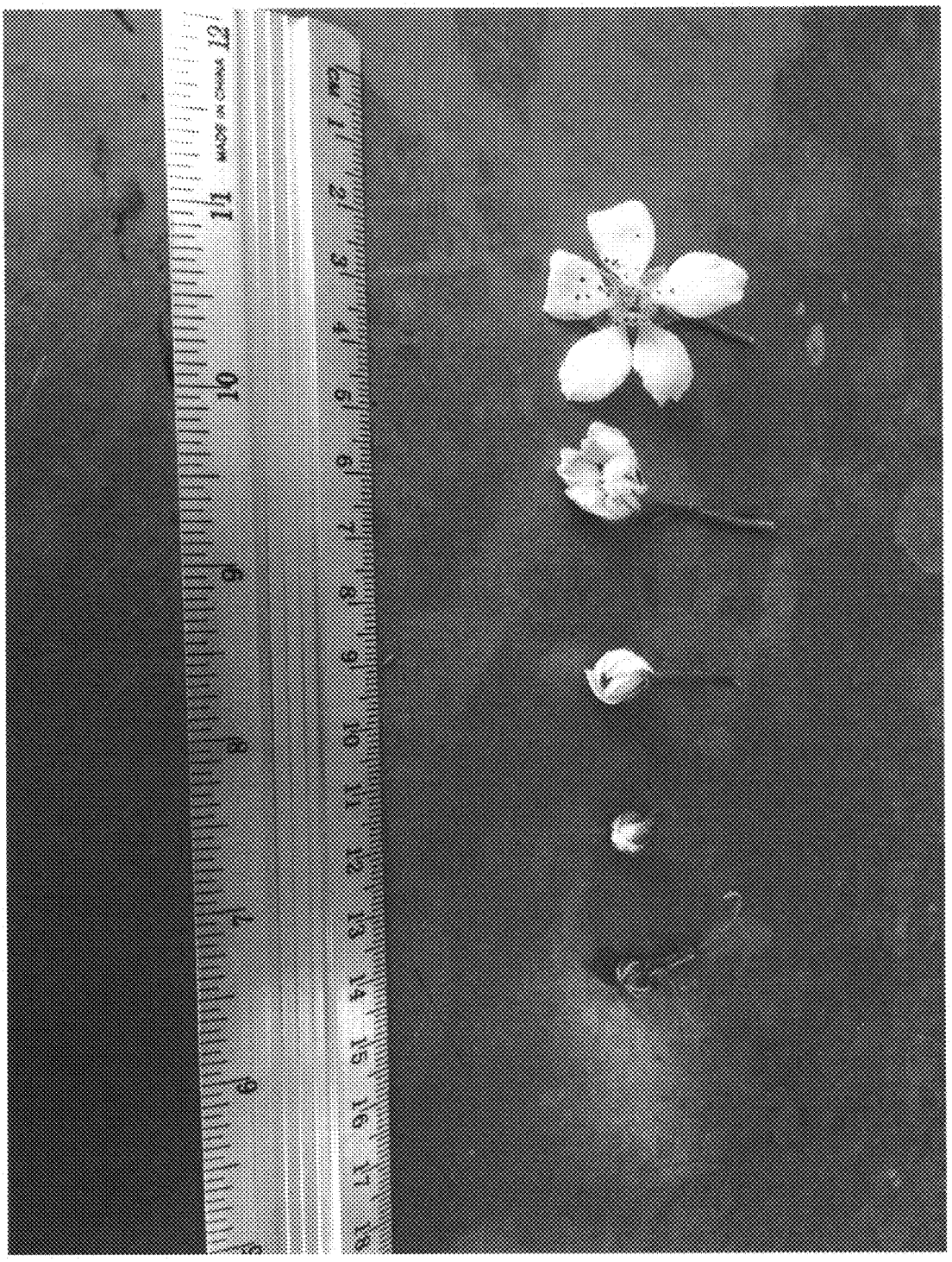
FIG. 2 illustrates typical flowers of variety 'DrisBlackTwenty' at various stages of development.
Figure 3:
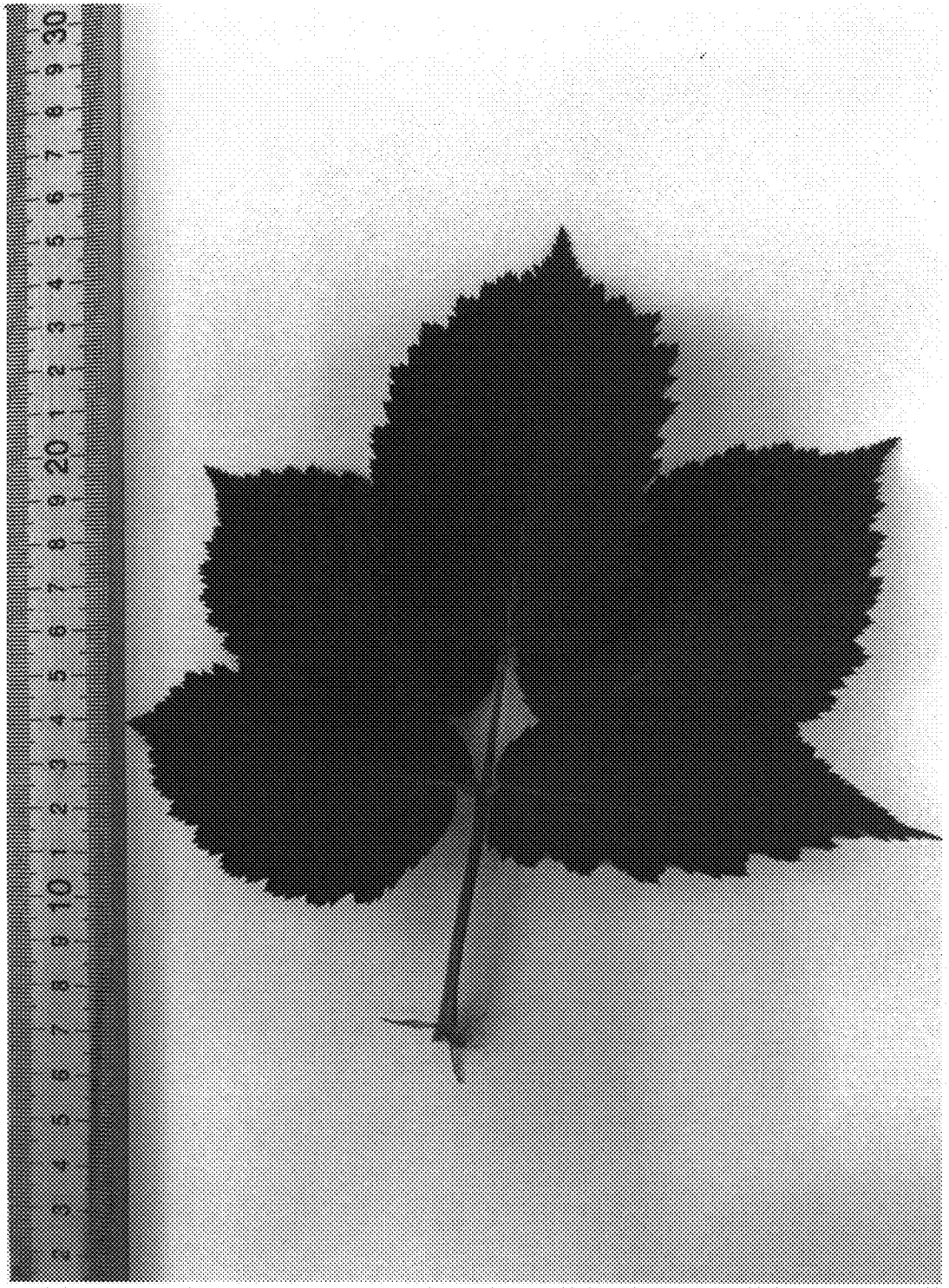
FIG. 3 illustrates a typical leaf of variety 'DrisBlackTwenty'.
Figure 4:
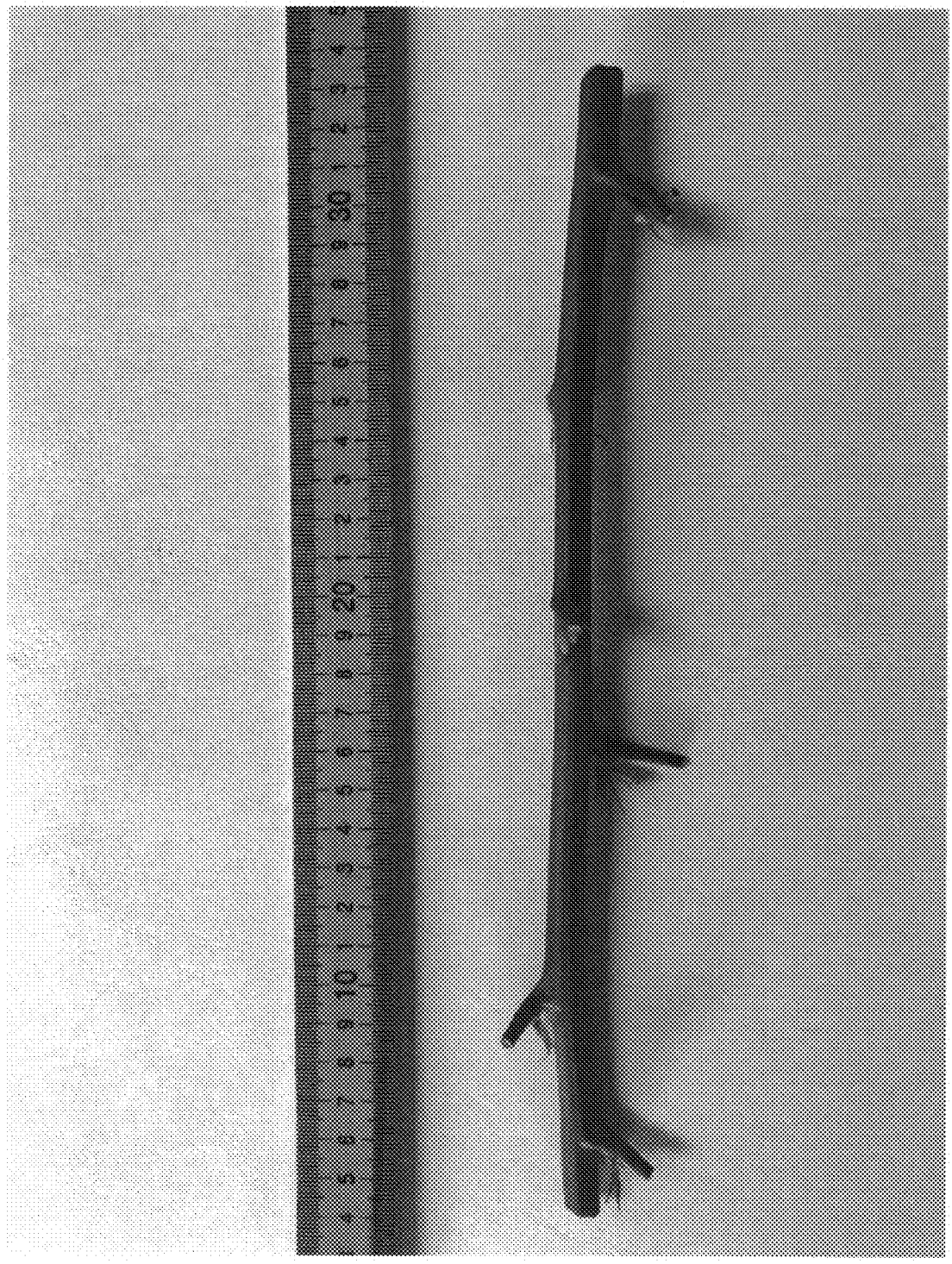
FIG. 4 illustrates a typical cane of variety 'DrisBlackTwenty'.
Figure 5:
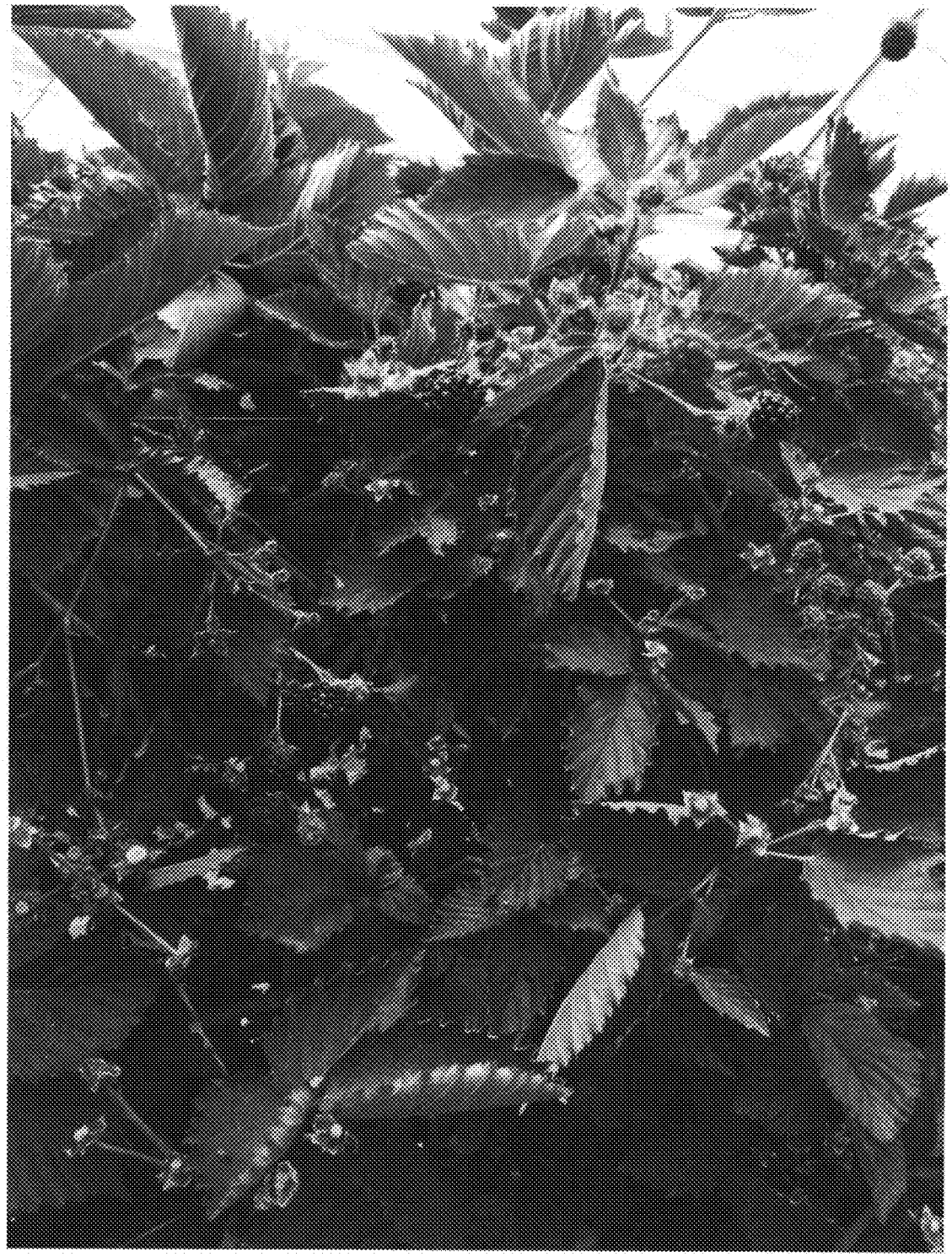
FIG. 5 illustrates a plant of variety 'DrisBlackTwenty'.

The following descriptions set forth the distinctive characteristics of 'DrisBlackTwenty'. The data that define these characteristics are based on observations taken in Los Reyes, Mexico from 2012 to 2018. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwenty' has not been observed under all possible environmental conditions. The botanical description of 'DrisBlackTwenty' was taken from plants that were three years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary, 2nd* edition by James G. Harris and Melinda Woolf Harris, unless where otherwise defined.

Classification:

*Family*.—Rosaceae.
*Botanical*.—*Rubus* L. subgenus *Rubus*.
*Common name*.—Blackberry.
*Variety name*.—'DrisBlackTwenty'.

Parentage:

*Female parent*.—"BN843.2' (unpatented).
*Male parent*.—'BL481.3' (unpatented).

Plant:

*Propagation*.—Root cuttings.
*Growth habit*.—Upright to semi-upright.
*Plant height*.—170 cm.
*Plant width*.—100 cm.

Canes:

*Fruiting lateral length* (*4th lateral from tip*).—53.4 cm.
*Number of fruits per fruiting lateral*.—11.4.
*Internodal distance*.—4.8 cm.
*Dormant cane*.—Anthocyanin coloration: Absent or very weak. Predominant distribution of branches: Only on upper half. Cross-section: Rounded to angular. Presence of spines: Absent.

Young shoots:

*Anthocyanin coloration* (*during rapid growth*).—Absent or very weak.
*Intensity of green color*.—RHS 143C (Strong yellow green).
*Young shoot length*.—56 cm.
*Young shoot diameter*.—0.743 cm.
*Young shoot texture*.—Medium rough.

Leaves:

*Terminal leaflet*.—Length: 77.44 mm. Width: 57.28 mm. Length/width ratio: 1.35. Lobing: Absent. Shape in cross-section: V-shaped. Undulation of margin: Weak.
*Lateral leaflets* (*basal pair*).—Length: 57.53 mm. Width: 41.99 mm. Length/width ratio: 1.37.
*Rachis length between terminal leaflet and adjacent lateral leaflets*.—25.54 mm.
*Petiole*.—Length: 59.63 mm. Diameter: 1.46 mm. Petiole color: RHS 144A (Strong yellow-green).

*Leaflet*.—Type of incision of margin: Bi-serrate. Leaflet shape: Ovate. Leaflet texture: Soft medium. Leaflet color of lower side: RHS 146A (Moderate olive green).

*Leaf*.—Predominant number of leaflets: 5. Type: Palmate. Intensity of green color of upper side: RHS 139A (Dark green). Leaf arrangement: Alternate. Leaf venation pattern: Dichotomous. Leaf vein color: RHS 144A (Strong yellow-green). Approximate date of leaf bud burst: January-April.

*Stipule*.—Stipule length: 0.692 cm. Stipule width: 0.09 cm. Stipule texture: Medium hairy. Stipule color: RHS 138B (Moderate yellow-green).

Flowers:

*Diameter*.—45.60 mm.

*Petal*.—Length: 24.20 mm. Width: 15.34 mm. Length/width ratio: 1.57. Color: RHS 155C (Greenish white) for both upper and lower sides of the petal. Number of petals per flower: 5. Petal texture: Soft medium. Shape of apex: Rounded. Shape of base: Cuneate. Petal margin: Retuse.

*Number of flowers observed at 3rd node from tip of lateral*.—2.4.

*Number of flowers per panicle*.—9.

*Pedicel*.—Length: 48.60 mm. Diameter: 1.24 mm. Pedicel color: RHS 137B (Moderate olive green).

*Sepal*.—Sepal length: 0.733 cm. Sepal width: 0.124 cm. Sepal texture: Soft medium. Sepal color: RHS 138A (Moderate yellowish green).

*Stigma*.—Stigma length: 0.00349 mm. Stigma width: 0.00328 mm. Stigma shape: Capitate. Stigma color: RHS 144B (Strong yellow-green).

*Style*.—Style length: 3.31 mm. Style width: 0.015 mm. Style shape: Elongate. Style color: RHS 145B (Light yellow-green).

*Ovary*.—Ovary length: 0.12 mm. Ovary width: 0.045 mm. Ovary shape: Capitate. Ovary color: RHS 134B (Strong yellowish green).

*Stamen*.—Stamen length: 5.8 mm. Stamen width: 0.25 mm. Stamen shape: Tetradynamous. Stamen color: RHS 155B (Yellowish white).

*Anther*.—Anther length: 1.33 mm. Anther width: 0.99 mm. Anther shape: Elongate. Anther color: RHS 155B (Yellowish white).

*Pollen*.—Pollen diameter: 0.00025 mm. Pollen shape: Oblate spheroidal. Pollen color: RHS 8B (Light greenish yellow).

*Peduncle*.—Peduncle diameter: 0.85 mm. Peduncle color: RHS 138A (Moderate yellow-green).

*Flower bud*.—Bud length: 6.91 mm. Bud width: 5.65 mm. Bud shape: Oblong. Bud color: RHS 144C (Strong yellow-green).

*Time of beginning of flowering*.—August-September.

*Duration of flowering*.—45 days.

Fruit:

*Length of mature fruit*.—33.36 mm.

*Diameter of mature fruit*.—26.09 mm.

*Ratio of fruit length to width*.—1.3.

*Average number of drupelets per fruit*.—109.

*Drupelet diameter*.—2.24 mm.

*Fruit weight*.—9.2 g/fruit.

*Soluble solids* (*in brix*).—16.2%.

*Titratable acidity* (*as citric acid*).—0.93%.

*Seed weight*.—0.006 g/seed.

*Seed diameter*.—2.03 mm.

*Seed shape*.—Elliptic.

*Seed color*.—RHS 146B (Light yellow-green).

*Shape of fruit in longitudinal section*.—Medium ovate.

*Immature fruit color*.—RHS 146A (Green).

*Maturing fruit color*.—RHS 185A (Purple).

*Mature fruit color*.—RHS 202A (Black).

*Fruiting on current year's cane*.—Absent.

*Harvest interval on previous year's cane*.—October-June.

*Yield*.—18,000 kg/hectare to 22,500 kg/hectare of fruit per season from 9-month-old plants when grown in Los Reyes, Michoacan, Mexico.

*Date of first fruit pick*.—September 24.

*Date of last fruit pick*.—December 31.

*Market use of fruit*.—Fresh market.

*Shipping and storage characteristics*.—Following harvest, fruit can be stored for 10 days if maintained under cooled temperatures (e.g. at 2° Celsius) that are standard for blackberry storage.

Resistance to diseases, pests, and abiotic stress:

*Spotted-wing drosophila* (*Drosophila suzukii*).—Moderately susceptible.

*Powdery mildew* (*Podosphaera macularis*).—Moderately susceptible.

*Fusarium wilt* (*Fusarium oxysporum*).—Resistant.

COMPARISONS TO PARENTAL AND COMMERCIAL BLACKBERRY VARIETIES

'DrisBlackTwenty' differs from the proprietary female parent 'BN843.2' (unpatented) in that 'DrisBlackTwenty' has higher vigor compared to 'BN843.2'. Moreover, 'DrisBlackTwenty' differs from the proprietary female parent 'BN843.2' in that 'DrisBlackTwenty' is spineless, whereas 'BN843.2' is spiny.

'DrisBlackTwenty' differs from the proprietary male parent 'BL481.3' (unpatented) in that 'DrisBlackTwenty' has higher yield potential than 'BL481.3'.

'DrisBlackTwenty' differs from commercial variety 'Tupy' (also spelled 'Tupi', unpatented) in that 'DrisBlackTwenty' has no spines on dormant cane, absent or few number of glandular hairs on young shoot, a V shape of terminal leaflet in cross-section, and a medium ovate fruit shape in longitudinal section. In contrast, 'Tupy' has spines present on dormant cane, medium number of glandular hairs on young shoot, a U shape of terminal leaflet in cross-section, and a circular to medium ovate fruit shape in longitudinal section.

'DrisBlackTwenty' differs from commercial variety 'DrisBlackSeventeen' (U.S. Plant Pat. No. 31,291) in that 'DrisBlackTwenty' has an upright to semi-upright plant growth habit, no spines on dormant cane, absent or few number of glandular hairs on young shoot, and early beginning of fruit ripening on previous year's cane. In contrast, 'DrisBlackSeventeen' has a semi-upright plant growth habit, spines present on dormant cane, many glandular hairs on young shoot, and medium beginning of fruit ripening on previous year's cane.

What is claimed is:

1. A new and distinct variety of blackberry plant designated 'DrisBlackTwenty' as shown and described herein.

* * * * *